United States Patent [19]

Lukenbach et al.

[11] Patent Number: 5,980,871
[45] Date of Patent: *Nov. 9, 1999

[54] SUNSCREEN COMPOSITIONS

[75] Inventors: Elvin R. Lukenbach, Flemington; Prakash Naik-Satam, Bloomfield, both of N.J.; Jean Holland, Doylestown; Curtis Cole, Langhorne, both of Pa.; Ralph Stutzman, San Antonio, Tex.

[73] Assignee: Johnson & Johnson Consumer Companies, Inc., Skillman, N.J.

[*] Notice: This patent is subject to a terminal disclaimer.

[21] Appl. No.: 08/660,130

[22] Filed: Jun. 7, 1996

Related U.S. Application Data

[63] Continuation-in-part of application No. 08/495,734, Jun. 8, 1995.

[51] Int. Cl.$^6$ .............................. A61K 7/42; A61K 7/00; C09C 1/36; C01G 23/047
[52] U.S. Cl. ............................ 424/59; 106/436; 423/610; 424/60; 424/400; 424/401
[58] Field of Search ................................. 424/59, 60, 400, 424/401; 423/610; 106/436

[56] References Cited

U.S. PATENT DOCUMENTS 5,207,998  5/1993  Robinson et al. ......................... 424/59

FOREIGN PATENT DOCUMENTS

WO 90/11067  10/1990  WIPO .
WO 94/04131  3/1994  WIPO .

*Primary Examiner*—Shelley A. Dodson

[57] ABSTRACT

This invention relates to novel sunscreen compositions containing inorganic sunscreen agents, anionic emulsifiers and an oil component which permit the use of low amounts of inorganic sunscreen agents in the compositions while achieving high sun protection factors or the use of high amounts of inorganic sunscreens for very high sun protection factors without whiteness.

19 Claims, No Drawings

SUNSCREEN COMPOSITIONS

RELATED APPLICATIONS

This application is a continuation-in-part of U.S. Ser. No. 08/495,734, filed Jun. 8, 1995, and hereby incorporates by reference that application and the subject matter therein into this application.

FIELD OF THE INVENTION

This invention relates to new and useful ultraviolet radiation sunscreen agents and compositions displaying enhanced protection and to methods of protecting human skin against the potentially harmful effects of sunlight.

BACKGROUND OF THE INVENTION

Although a tan has long been considered a status symbol indicative of good health and the ability to secure sufficient leisure time to enjoy outdoor activities such as swimming, tennis, golf, skiing and the like, it has become very evident that excessive exposure of the human skin to sunlight is harmful.

It is well documented that human skin is sensitive to sunlight and artificial light containing radiation of wavelengths between about 290 nanometers (nm) and 400 nm. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years, concern has also been expressed regarding ultraviolet radiation of wavelengths above 320 nm (UV-A region) and the adverse effects of such radiation on human skin. The radiation between 320 and 400 nm also contributes to the premature aging of the skin. In addition, recent studies indicate that chronic sun exposure limits the immuno-response of the skin. There is also evidence that a tan will offer some protection against burning but is quite ineffectual against other types of solar damage.

Growing public awareness that the enjoyment of outdoor activities must go hand in hand with adequate sun protection has led to an unprecedented growth in the area of sunscreen products. A desirable sunscreen product should have the following attributes: protection in both the UV-A and UV-B ultraviolet radiation ranges; maintenance of coverage, i.e., waterproof and perspiration proof; application and use convenience, i.e., ease of application, invisibility, non-staining and non-greasy; and freedom from irritation as a result of its ingredients, in particular, its active sunscreen ingredients. Of recent interest in this area have been some concerns over the irritancy and sensitization problems that may occur in some individuals utilizing sunscreen products with high SPF values containing organic sunscreen agents.

The effectiveness of a sunscreen product is indicated by its sun protection factor (SPF). The sun protection factor is the ratio of the amount of exposure (dose) required to produce a minimal erythema reaction in protected skin to the amount required to produce the same reaction in unprotected skin. The absolute dose differs from person to person and is largely dependent on one's genetic predisposition and ethnic origin. If a person would normally require ten minute exposure to sunlight to develop a minimal erythema reaction, this person when using an SPF 15 sunscreen product should be able to tolerate up to 150 minutes of sunlight before developing a minimal erythema. Recent public awareness of the problems of exposure to sunlight has led to a demand for sunscreen products with high SPF values, i.e., at or above SPF 8.

Ease of application and cosmetic appeal, on the other hand, are important in formulating sunscreen compositions. These characteristics rely on subjective evaluations such as visual and tactile impression by the user. Consumer research studies indicate that a sunscreen formulation should rub in easily, leave the skin non-sticky and, above all, should be invisible on the skin after application. Sunscreen compositions containing organic sunscreen agents have been found, in some cases, to be irritating to the skin. Therefore, use has been made of inorganic sunscreen agents, such as titanium dioxide and zinc oxide.

For example, Japanese Patent Application No. 1981-161,881, describes cosmetics containing 0.1–40% of ultrafine divided titanium oxide with a particle size of 10–30 nanometers (nm) which has been rendered hydrophobic. It indicates that when hydrophobically treated titanium oxide with a particle size of 10–30 nm is blended into cosmetic base materials, it transmits visible light but reflects and scatters the harmful ultraviolet rays. It has been found that when these titanium dioxide compositions are utilized as a sunscreen agent in sunscreen compositions, it may result in the loss of one of the most desired properties of such compositions, i.e., invisibility.

U.S. Pat. No. 5,028,417, issued Jul. 2, 1991, describes sunscreen compositions containing microfine titanium dioxide. The particle size of the titanium dioxide is required to be less than 10 nm. It also states that other sunscreen agents can be utilized with the titanium dioxide.

U.S. Pat. No. 5,340,567, issued Aug. 23, 1994 describes a sunscreen composition comprising a synergistic combination of titanium dioxide having a particle size of less than about 35 nm and zinc oxide having a particle size of less than about 50 nm with titanium dioxide and zinc oxide being present at given ratios.

German Patent No. 3,642,794 (1987) describes a cosmetic composition for preventing sunburn which contains 1–25% zinc oxide of a particle size of 70–300 microns. It further indicates that the composition may also contain titanium dioxide of a particle size of 30–70 microns. This composition is undesirable due to its unaesthetic whiteness characteristics at high SPF levels.

U.S. Pat. No. 5,188,831, issued Feb. 23, 1993, describes sunscreen compositions wherein the sunscreen effect is obtained from a blend of oil-dispersible ultrafine titanium dioxide and water-dispersible titanium dioxide. However, the SPF level obtained is only of 10 with a total concentration of titanium dioxide of 5.0% w/w.

World Patent Application WO 90/06103, published Jun. 14, 1990, describes titanium dioxide sunscreens where the microfine titanium dioxide particles are coated with a phospholipid, either through the use of a powder mill or through the making of a dispersion in an oil phase containing the phospholipid with a high shear mixer. The phospholipid coated titanium dioxide is then incorporated into sunscreen compositions. A high efficiency is claimed: the data presented shows SPF values of up to 11 for a 3.75% titanium dioxide concentration and up to 25 for a 7.5% concentration of titanium dioxide. The use of high shear mixer or a powder mill is a complicated and energy intensive process.

EP 535972 A1, published Apr. 7, 1993 describes a method of preparing sunscreens in which a dispersion of zinc oxide and/or titanium dioxide particles in an oil is formed by milling.

EP 619999 A2, published Oct. 19, 1994 describes an aqueous dispersion of particulate metallic oxide of particle size less than 200 nm mixed with an emulsifier and an oil phase and also an organic hydrophobic sunscreen to form an o/w emulsion. The resulting sun protection composition has a higher SPF than would be expected if there was only an additive effect. However, the titanium dioxide alone at 4% yielded a SPF of only 7 to about 11.

EP 628303, published Oct. 19, 1994 describes a process for preparing a sunscreen composition. It consists of mixing sunscreen particles of metallic oxide less than 200 nm dispersed in an oil with one or more emulsifier and/or organic sunscreens. The resulting sunscreen composition is claimed to have a SPF value considerably higher than expected. The high SPF is only obtained when a metallic oxide is blended with an organic sunscreen. In fact, when no organic sunscreen is used, the SPF value is only about 7.

WO 93/11742 describes sunscreen compositions comprising titanium dioxide and iron oxide of particle size less than 200 nm preferably coated with a phospholipid.

An article published in DCI in September 1992 by Tioxide Specialties Ltd. describes various ways of incorporating oil or water dispersions of titanium dioxide in emulsions. However, no data is given on the resulting SPF values.

An article published in Cosmetics and Toiletries, Vol. 107, October 1992, describes various ways of formulating with a physical sunblock. The discussion focuses on using titanium dioxide in a dispersion or using an emulsifier which is also an effective dispersing agent for titanium dioxide. It states that SPF's far above 20 can be achieved. However, no examples are given, nor does the article mention the specific sunscreen components or their compositions.

A brochure published by the Tioxide Company on Mar. 15, 1994, discloses inorganic sunscreens of high SPF values obtained without the addition of any organic sunscreens. When measured, the SPF of the sunscreen compositions was indeed that described. However, when the titanium dioxide concentration was measured, it was at least twice what was claimed.

U.S. Pat. No. 5,498,406 describes sunscreen compositions in an oil-in-water emulsion containing both organic and inorganic sunscreens and comprising long chain ($C_{25-45}$) alcohols for stabilization of the emulsion. This composition relies predominantly on the organic sunscreen actives. While the authors mention the use of stearic acid as a part of the oil in water composition, they teach against the use of stearic acid in stabilizing the titanium dioxide without $C_{22-45}$ alcohols.

A sunscreen was marketed in the late 1980's under the trademark SUNDOWN®, which contained both organic and inorganic sunscreen ingredients. In addition, it contained Velsan D8P3 and isostearic acid. However, it was not an efficient sunscreen, despite the addition of both organic and inorganic sunscreen ingredients.

OBJECTS OF THE INVENTION

It is, therefore, an object of the present invention to provide improved sunscreen agents and compositions.

It is another object of the present invention to provide sunscreen compositions containing sunscreen agents that overcome the disadvantages of heretofore available materials and provide adequate and safe protection for human skin.

It is a further object of this invention to provide methods of protecting human skin against the harmful effects of sunlight.

These and other objects and features of the present invention will become readily apparent to one skilled in the art from the detailed description given hereinafter.

SUMMARY OF THE INVENTION

The foregoing objects and other features and advantages of the present invention are achieved by sunscreen compositions containing inorganic sunscreen agents as the active ingredients. More particularly, the present invention relates to sunscreen compositions containing titanium dioxide and, optionally, zinc oxide of preferred particle size ranges, and in preferred amounts and ratios as the sunscreen agents.

These specific compositions permit the use of much lower amounts of the sunscreen active ingredients than previously achievable while still achieving the desired high SPF values for the compositions and without the unsightly whiteness which occurs in prior sunscreen compositions at concentrations above about 5%. In the sunscreen compositions of this invention, considerably higher concentrations of titanium dioxide may be used without incurring a whitening effect, e.g., even up to 15% with acceptable appearance, or possibly higher.

Furthermore, our invention does not rely upon the use of hydrophilic titanium dioxide preparations as required in the above noted patent, nor are energy intensive processes such as powder milling, nor are organic sunscreen actives required for the high efficacy.

The compositions of this invention are oil-in-water emulsions containing at least the following components:

(a) an inorganic sunscreen agent, such as titanium dioxide or zinc oxide or a mixture thereof;

(b) an anionic emulsifier selected from the following group: salts of saturated fatty acids and/or salts of straight-chain fatty acids, alkyl sulfates, alkyl sulfosuccinates and alkyl phosphates; and (c) an oil component containing a carrier oil and at least one emollient.

The compositions of this invention provide sunscreen formulations having an SPF of at least 10 with a concentration level of titanium dioxide of about 4%. The compositions of this invention exhibit extremely efficient uses of sunscreen components, particularly titanium dioxide. The compositions of this invention therefore may be formulated so as to contain relatively smaller amounts of titanium dioxide than used heretofore at a given SPF level.

Essentially, the compositions of this invention are easily made by simple mixing and provide an excellent dispersion of the inorganic sunscreen agent throughout the composition, thus ensuring even skin coverage. They are substantially invisible upon application to the skin.

DETAILED DESCRIPTION OF THE INVENTION

The sunscreen compositions of this invention yield highly effective ultraviolet—(UV) blocking capabilities; that is, a given level of protection is provided with a significantly lower concentration of titanium dioxide than previously obtained using commercially available powdered titanium dioxides. They do not require the unusual processing methods previously necessary to disperse the titanium dioxide into an oil, such as preparation of sub-batch mill bases, high shear mixing or milling, or applying such milling procedures to the final product formulation. Typical titanium dioxide sunscreen compositions of SPF 15 require levels of titanium dioxide that impart a significant whitening effect to the skin; the compositions of this invention, minimize this disadvantage.

The compositions of this invention are oil-in-water emulsions that are cosmetically superior to conventional inorganic sunscreen preparations, including water-in-oil titanium dioxide-only formulations, at equivalent SPF ratings, due to the low levels of titanium dioxide needed in the invention system. The compositions of this invention can be used for sun protection in daily wear or facial products as well as recreational situations. Because of the efficiency of the system, the inventive formulations are significantly lower in cost than other sunscreen systems.

There are several ingredients that contribute to the unexpectedly high efficiency of the compositions' blocking of UV radiation. These elements include the following materials:

The compositions of this invention should include one or more of a select group of anionic emulsifiers. In particular, salts of certain fatty acids are useful in the formulations of this invention, preferably salts of saturated fatty acids and/or salts of straight-chain fatty acids. Alkali metal salts, alkali earth metal salts and amine salts are more preferable for use in the compositions of this invention. For example, stearic acid and its salts are useful as emulsifiers in the compositions of this invention, while the use of isostearate salts tends to produce a composition which is not very efficient in the use of sunscreen. Likewise, oleate salts are not useful as they are unsaturated and do not result in efficient sunscreen compositions.

More particularly, the following anionic emulsifiers are useful in the compositions of this invention: sodium stearate, sodium lauryl sulfate, DEA cetyl phosphate, sodium dioctyl sulfosuccinate and the like. Most preferably, the emulsifier should be sodium stearate. While it is not fully understood why some salts of fatty acids result in an inventive composition, it is theorized that salts of straight-chain fatty acids, (the fatty acids having a relatively high melting point, above 70° C. or higher), are preferred due to their structure. For example, salts of branched or unsaturated fatty acids are not acceptable for use in the compositions of this invention.

The anionic emulsifiers should be present in the compositions of this invention in an amount from about 0.01 to about 10%, more preferably 0.1 to about 7% and most preferably from about 0.5 to about 5%. There may be additional emulsifiers present in the compositions of this invention, such as nonionic emulsifiers known to those of ordinary skill in the art, such as sorbitan esters and ethoxylated sorbitan esters, ethoxylated fatty acids, fatty alcohols and ethoxylated fatty alcohols, fatty glyceride esters and ethoxylated fatty glyceride esters and the like. However, there should be at least one anionic emulsifier present in order to achieve the products of this invention. The fatty acid salt emulsifiers may be added to the composition as the salt, or the salt may be formed in situ.

A carrier oil should also be present in the compositions of this invention. It may be selected from the group of benzoic acid fatty alcohol esters, alkoxylated fatty alcohols and polyether interrupted fatty acid esters. The benzoic acid fatty alcohol esters described are commercially available under the trade name Finsolv, e.g. Finsolv TN, available from Finetex. The alkoxylated fatty alcohols are available under a variety of sources such as Eumulgin L and Eumulgin B2 from Henkel, Sandoxylates from Clariant, Marlox FK86 from Huls America, Procetyl AWS from Croda Chemicals and others.

Preferably, such carrier oils should be selected from the group of polyether interrupted fatty acid esters. More preferably, the carrier oil should be a $C_8$ to $C_{22}$ fatty alkyl (optionally polypropylenoxy) polyethylenoxy carboxylate ester, the ester having an alkyl group which has from one to twenty-two carbon atoms, optionally straight or branched or can contain a phenyl group. Most preferably, the carrier oil should be a isopropyl PPG-2 isodeceth-7 carboxylate, such as Velsan D8P3 or other commercially available materials sold by Clariant under the Velsan trade name. Other similar structures include Hetester PHA available from Bernel.

Preferably, the carrier oil should be present in the composition in an amount of between about 0.1% and about 10%. More preferably, it should be present in the amount of between about 1% and about 5%. Most preferably, it should be present in the amount of between about 2% and about 3%.

Preferably, the oil phase should contain at least two materials, the carrier oil and a conventional emollient known to those of ordinary skill in the art as useful in sunscreen products, such as mineral oil, ester oils, vegetable oils, silicones, synthetic emollients such as fatty acid esters and the like. This emollient should be present in the formulation in a ratio to the carrier concentration of from about 1:1 to about 3:1, most preferably, about 2:1. The carrier oil and the emollient should compose from about 2% to about 20% of the composition by weight.

The third element which should be present in the compositions of this invention is an inorganic sunscreen compound, such as titanium dioxide, zinc oxide or combinations thereof. Preferably, titanium dioxide should be used having a primary particle size from of less than about 300 nm in diameter. It should be present in the composition in the amount of from about 2% to about 25%. More preferably, it should be present in the amount of from about 2% to about 15%. Most preferably, it should be present in the amount of from about 3% to about 10%. The inorganic sunscreen compound should be oil dispersible, and may be present with or without surface coating.

The ratio of titanium dioxide to the weight of the carrier oil and the emollient combined should be from about 0.3:1 to about 1:1. Most preferably, the ratio should be between about 0.5:1 and 2:3. For example, a composition containing 15% titanium dioxide, 8.33% Velsan D8P3, 12.5% Miglyol 812 and the remainder of the composition identical to that of Example 1 below, results in a sunscreen composition having an SPF of 43. The whiteness value of this composition is acceptable and is only slightly whitening on the skin.

In the case where salts of fatty acids are used care should be taken to keep the pH of the compositions of this invention at a level above about 5, more preferably, above about 5.5. Maintaining the pH at this level will ensure that these anionic emulsifiers remain in the salt form, which is important in retaining the stability and efficacy of the composition. When the other listed anionic emulsifiers are used, the stability and efficacy of the composition is not affected below said pH limitations.

Additionally, the usual elements of a modern sunscreen emulsion system, such as a polymeric thickener/stabilizer, one or more additional emollient oils, microbial preservatives, waterproofing agents, antioxidants, fragrance, humectant, and of course the water vehicle are utilized without known selection or restraint.

The base formulation of the compositions of this invention may also be used as carrier compositions for active topical agents having dermatological effects, including depigmentation agents, anti-aging ingredients, antifungal agents, antimicrobial agents, insect repellents and the like. For example, depigmentation agents can include magnesium ascorbyl phosphate or hydroquinone. Anti-aging agents can include retinoid compounds and alpha-hydroxy acids. Antifungal agents which can be included in the compositions of this invention include azole compounds including ketoconazole and the like. Antimicrobial agents can include triclosan. Insect repellent fragrances can be included in the compositions of this invention. Other products known to those of ordinary skill in the art may be delivered to the skin using the compositions of this invention. The compositions of this invention would then have dual-action capability, as they would contain both sunscreen agents and other actives for protecting and/or treating the skin.

The compositions of this invention can be incorporated into various cosmetic and personal care products such as hand and body lotions, oils, ointments, lip balm products, facial cosmetics and the like.

The sunscreen compositions of this invention may be prepared using one of at least two methods: a two-vessel method, in which the oil and water phases are individually prepared, and a one-vessel method into which all ingredients are added in selected, specific order. Any of these processes will produce a smooth, uniform, white to light ivory emulsion.

In accordance with the two-vessel process, a water phase is prepared by measuring deionized water into a beaker and mixing. The elements of the water phase, including emulsifiers and humectants, chelators, thickeners, waterproofing agents, neutralizing agents and antioxidants should be added and the solution heated. The anionic emulsifier may be placed into the water phase or into the oil phase, depending upon the nature of the emulsifier. The oil phase is prepared separately in another vessel, including the anionic emulsifier, carrier oil, emollient and inorganic sunscreen agent. The two phases are then held at a relatively high temperature and mixed.

More specifically, in the two-vessel process, the water phase is prepared by measuring deionized water into a beaker and mixing. Next, Carbopol 940 (available from B. F. Goodrich of Cincinnati, Ohio) should be added and the composition mixed until properly hydrated. Propylene glycol and EDTA should then be added and the composition mixed until a homogeneous solution is achieved. The solution should then be heated to 70–80° C. The solution should be maintained at 70–80° C. for phasing.

The oil phase is then prepared by adding the following ingredients into a beaker: BHT, Velsan D8P3 (available from Clariant Corporation, Charlotte, N.C.), Stearic Acid, Cetyl Alcohol and Miglyol 812 (available from Huls Company of Piscataway, N.J.). The beaker should be placed in a water bath on an electric hot plate. The ingredients should be heated to about 80° C. or until melted. The titanium dioxide should be added slowly and the composition stirred at high speed until homogeneous. The mixture should be maintained at about 80° C. until phasing.

The composition may then be phased by adding the Oil Phase to the Aqueous Phase and mixing, holding the temperature at about 80° C. for 5 minutes. Sodium hydroxide should then be added (as a 10% solution) and the composition mixed for 5 minutes at high speed. Next, the mixing speed should be reduced and cooling begun. When the temperature of the batch reaches 40–45° C., Dowicil 200 (a 33% solution of Quaternium 15 available from Dow Chemical Company, Dearborn, Mich.) is added and, optionally, fragrance. The pH should be checked and adjusted to a value above pH 5.0 with a 10% solution of Sodium Hydroxide, if needed. Deionized water may be added as required to bring the batch to final weight. When the temperature of the batch reaches 28–32° C., mixing and cooling may be discontinued.

In the one-vessel process, the water and oil phases may be made in the same vessel, provided that the components are added in an appropriate order. For example, the water phase should be created first, adding water and optionally certain emulsifiers which are compatible with the water phase to the vessel. The vessel should be heated to about 85° C. to about 95° C. Once the temperature reaches this level, the oil phase components may be added, including, optionally, the anionic emulsifier if it is oil-phase compatible and the carrier oil, as well as any additional oil-phase emulsifiers, antioxidants and emollients that may be desired. The temperature should be maintained at this level for about 15 minutes, and the inorganic sunscreen agent added slowly, and the composition mixed for a period of time of at least about 30 minutes. After cooling the pH may then be checked and adjusted if needed, Dowicil, a preservative added as well as optional fragrance.

More specifically, deionized water may be added to a beaker to which is slowly added Carbopol 940. Next, EDTA is added and the composition mixed at high speed for 15–20 minutes or until the Carbopol is properly hydrated. Heating of the mixture to 92–95° C. should be begun and the required amount of Propylene Glycol added during this time. When the temperature reaches 92–95° C., BHT, Velsan D8P3, Stearic Acid, Cetyl Alcohol and Miglyol 812 are added. The temperature of the mixture should be maintained at about 92–95° C. for about 15 minutes. Then, titanium dioxide should be added and the composition mixed for 30 minutes. Sodium Hydroxide (as a 10% solution) should be added and the composition mixed for 30 minutes at 88–92° C. The composition should be cooled and, at 40° C., Dowicil 200 solution added as well as optional fragrance. The pH should be adjusted to above pH 5.0 with Sodium Hydroxide. Finally, sufficient water should be added to bring the batch to the target weight.

The following examples serve as illustrations of the compositions of this invention, however, they do not limit the scope of the invention described herein.

EXAMPLE 1

743.07 ml deionized water was added to a beaker. 2.5 grams Carbopol 940 (available from B. F. Goodrich of Cincinnati, Ohio) was then slowly added to the beaker. 1.0 gram Disodium EDTA was then added and the composition mixed at high speed for 15–20 minutes or until the Carbopol was properly hydrated. The mixture was heated to 92–95° C. and 30 grams of propylene glycol was added. When the temperature reached 92–95° C., 0.5 g BHT, 25 grams Velsan D8P3 (available from Clariant Corporation, Charlotte, N.C.), 50 grams stearic acid, 10 grams cetyl alcohol and 37.5 grams Miglyol 812 (available from Huls Company of Piscataway, N.J.) were added. 45 grams titanium dioxide MT-100T (an aluminum stearate coated microfine titanium dioxide available from Tri-K Industries, Emerson, N.J.), was then added to the vessel and the composition mixed for 30 minutes at 88–92° C. Cooling began and, when the composition reached 40° C., 3 grams Dowicil 200 (a 33% solution of Quaternium 15) was added, as well as 2.5 grams of fragrance. The pH was adjusted to 8–8.5 with 49.93 grams of 10% solution of sodium hydroxide (target pH is 8.25). Finally, sufficient deionized water was added to bring the batch to the target weight.

The in-vitro SPF (Sun Protection Factor) of this composition was measured using the system described by Cole and VanFossen [Cole, C., VanFossen R., (1990) In-vitro model for UVB and UVA protection. In: Sunscreens: Development, Evaluation and Regulatory Aspects, N. Shaath and N. Lowe Eds., Marcel Dekker Pub. New York, N.Y.]. Briefly, this system consists of the measurement of transmission of solar simulated UV radiation through composition (2.0 mg/cm$^2$) applied to the substrate, Transpose™ tape in this instance. The system consists of an optical sensor that is only sensitive to sunburning radiation and has a sensitivity spectrum similar to the human erythema sensitivity spectrum. The SPF is the ratio of the optical signal through the substrate without sunscreen divided by the optical signal through the substrate coated with the sunscreen. The system is calibrated against a series of sunscreens of known SPF (4 through 36) determined in-vivo using the FDA monograph method (Federal Register, Aug. 25, 1978, Sunscreen drug products for over-the-counter human drugs. pp 38206–38269.) The resulting SPF of the composition of Example I above is 16.9 and the composition is aesthetically satisfactory and stable.

EXAMPLES 2–13

In the next series of examples the use of titanium dioxides of different origins and/or types of coating at the same concentration of 4.5% was investigated. The compositions were all made in accordance with the method set forth in Example 1, having the same components in the same concentrations but for the varied component. The results are set forth in Table I.

TABLE I

Effect of TiO$_2$ Coating on the SPF (4.5% TiO$_2$)

| TiO$_2$ Source | Surface Treatment | SPF |
| --- | --- | --- |
| (2) MT-100T (Tri-K Industries, Inc.) | Al, Stearic Acid | 16.9 |
| (3) MT-500B (Tri-K Industries, Inc.) | None | 13.6 9.9 |
| (4) SMT-100SAS (Tri-K Industries, Inc.) | Methyl hydrogen polysiloxane | 5.0 |
| (5) UV Titan M262 (Presperse, Inc.) | Alumina, Dimethicone | 18.0 12.0 |
| (6) UV Titan M212 (Presperse, Inc.) | Alumina, Glycerin | 8.5 |
| (7) P25 (Degussa) | None | 9.1 |
| (8) STT65C-S (Kobo) | None | 12.1 |
| (9) DM140 KSI (Kobo) | STT65C-S surface treated with silicone | 11.5 |
| (10) SJT-30D-S (Kobo) | Al, Si, Silicone | 3.8 |
| (11) STT-30S-L (Kobo) | Al, Stearic Acid | 7.3 |
| (12) TiO$_2$ (Hydrophobic) (Creative Polymers) | Methicone, Dimethicone | 12.0 |
| (13) TiO$_2$ (Hydrophilic) (Creative Polymers) | Dimethicone Copolyol | 7.7 |

EXAMPLES 14–17

In this series of examples, the concentration of titanium dioxide was varied and the resulting SPF was measured. The formulae are made in accordance with the method set forth in Example 1 and differ in concentration only as to the amount of titanium dioxide. The difference was made up with deionized water.

| MT-100T Titanium dioxide concentration | SPF |
| --- | --- |
| (14) 4.5% | 17.1 |
| (15) 6.0% | 25.3 |
| (16) 7.5% | 20.4 |
| (17) 15.0% | 43.1 |

EXAMPLES 18–38

The following examples are intended to show which anionic emulsifiers result in a high SPF. The compositions were identical to that of Example 1, except in that the anionic emulsifier was varied in accordance with the information set forth in Table II below. From the data presented in the Table II, it can be seen that dioctyl sodium sulfosuccinate, DEA cetyl phosphate (Amphisol) under the right circumstances, Sodium lauryl sulfate and Sodium stearate are all effective in yielding an SPF higher than 10.

TABLE II

Effect of Anionic Emulsifiers on the SPF

| | SPF |
| --- | --- |
| (18) Sodium Stearate (NaOH Neut.)-Stearic acid plus Sodium Hydroxide | 11.6 |
| (19) Sodium Stearate in water phase | 15.7 |
| (20) 5.0% Isostearic Acid no Brij 721, no Stearic Acid with Miglyol 812 and Velsan D8P3 | 4.5 |
| (21) 5.0% Isostearic Acid (added to H$_2$O + NaOH) 3.0% Brij 721 | 8.6 |
| (22) 5.0% Oleic Acid, no Stearic Acid, pH adj. | 6.1, 5.2 |
| (23) 5.0% Lauric Acid, no Stearic Acid | 6.4 |
| (24) 2.0% Amphisol with 3.0% Brij 721 and Stearic Acid, no pH adj. | 12.3 |
| (25) 2.0% Amphisol with Brij 721 and no Stearic Acid | 8.1 |
| (26) 2.0% Amphisol with Brij 721 and no Stearic Acid, no pH adj. | 15.1 |
| (27) 0.5% Sodium Lauryl Sulfate with Stearic Acid, 3.0% Brij 721, no pH adj. | 15.0 |
| (28) Avanel S150 (2.5%), Miglyol 812 (3.75%), Stearic acid (5.0%), no pH adj. | 5.1 (2.3) |
| (29) Avanel S150 (2.0%), Stearic Acid (0%), Velsan D8P3 (2.5%), Miglyol 812 (3.75%), Brij 721 (3%) | 3.2 (2.0) |
| (30) Avanel S150 (5.74%), Velsan D8P3 (0%), Miglyol 812 (0%) | 7.0 (2.6) |
| (31) 2.7% Brij 721, 0.3% Brij 72 and 0.5% Rewoderm S1333, no Stearic Acid, pH = 7 | 4.1 |
| (32) 2.7% Tween 60, 0.3% Span 60 and 0.5% Rewoderm S1333, no Stearic Acid, pH = 7 | 4.2 |
| (33) 3.0% Glucam E-20 Distearate and 0.5% Rewoderm S1333, no Stearic Acid, pH = 7 | 3.8 |
| (34) 3.0% Glucam SSE-20, 0.5% Rewoderm S1333, no Stearic Acid, pH = 7 | 3.5 |
| (35) 1.0% Lecithin, no Stearic Acid 3.0% Brij 721, no pH adj. | 3.0 |
| (36) Aerosol TO-75 with Stearic Acid, Brij 721, no pH adj. | 11.2 |
| (37) Aerosol TO-75 with Stearic Acid, Brij 721, 0.5% Sodium Stearate, no pH adj. | 16.2 |
| (38) Hamposyl C-30, no Stearic acid | 5.9 |

The brand names set forth above refer to the following compounds:
Brij 721: Non ionic surfactant: Polyoxyethylene 21 stearyl ether
Miglyol 812: Capric/caprylic triglyceride
Velsan D8P3: PPG-2 isodeceth-7 carboxylate
Rewoderm S-1333: Disodium ricinoleamido MEA sulfosuccinate
Amphisol: DEA Cetyl phosphate
Aerosol TO-75: Dioctyl sodium sulfosuccinate
Hamposyl is a sodium cocoylsarcosinate, an anionic emulsifier

EXAMPLES 39–46

The following examples 39–46 demonstrate that nonionic emulsifiers by themselves do not result in a high SPF. The compositions set forth below are identical to that of Example 1 except for the variations indicated in Table III below.

TABLE III

Effect of Nonionic Emulsifier on the SPF

| | SPF |
|---|---|
| (39) 6.0% Cetyl Alcohol, no Stearic Acid 3.0% Brij 721, and no pH adj. | 2.7 |
| (40) 5.0% Glyceryl Monostearate, 2.0% Tween 60, 1.0% Arlacel 60, no Stearic Acid, pH = 7 | 2.9 |
| (41) 5.0% Glyceryl Monostearate, 3.0% Brij 721, no Stearic Acid | 5.1 |
| (42) 2.7% Brij 721/0.3% Brij 72, no Stearic Acid, pH = 7 | 2.5 |
| (43) 2.7% Tween 60, 0.3% Span 60, no Stearic Acid, pH = 7 | 3.6 |
| (44) 3.0% Glucam E-20 Distearate, no Stearic Acid | 2.9 |
| (45) 3.0% Glucam SSE-20, no Stearic Acid | 3.3 |
| (46) 5.0% Glucam P-20, no Stearic Acid | 2.5 |

Tween 60 is a polyoxyethylene (20) sorbitan monostearate.
Arlacel 60 is a sorbitan monostearate.
Arlacel 165 is a glycerol monostearate and polyoxyethylene stearate.
Span 60 is a sorbitan monostearate.
Glucam E-20 distearate is a methylgluceth 20 distearate.
Glucam SSE-20 is an ethoxylated (20) methyl glucoside sequistearate.

EXAMPLES 47–90

The following Examples 47–90 set forth the importance of using carrier oils in the products of this invention in conjunction with emollient oils known to those of ordinary skill in the art and available commercially. They are similar to Example 1, varying only the oil component, as indicated below.

TABLE IV

Effect of Single Oils and Oil mixtures

| | SPF[1,2] |
|---|---|
| (47) Finsolv TN (6.25%) | 7.0 |
| (48) Finsolv TN (2.5%)/Miglyol 812 (3.75%) | 15.8 |
| (49) Finsolv TN (3.75%)/Velsan D8P3 (2.5%) | 16.4 (4.0), 18.4 (4.4) |
| (50) Finsolv TN (3.125%)/Mineral Oil NF (3.125%) | 9.1 (3.2) |
| (51) Finsolv TN (3.125%)/Cetiol 868 (3.125%) | 8.2 (2.9) |
| (52) Miglyol 812 (6.25%) | 8.9 (3.2) |
| (53) Velsan D8P3 (6.25%) | 10.0 (3.3) |
| (54) Procetyl AWS (6.25%) | 9.9 (3.4) |
| (55) Procetyl AWS (3.75%)/Velsan D8P3 (3.25%) | 16.8 (4.2) |
| (56) Procetyl AWS (3.75%)/Miglyol 812 (2.5%) | 10.6 (3.3) |
| (57) Procetyl AWS (3.125%)/Mineral Oil NF (3.125%) | 10.7 (3.2) |
| (58) Procetyl AWS (3.125%)/Citmol 316 (3.125%) | 11.6 (3.5) |
| (59) Isopropyl Myristate (6.25%) | 8.7 (2.8), 5.3 (2.4) |
| (60) Isopropyl Myristate (3.75%)/Velsan D8P3 (2.5%) | 13.0 (3.4) |
| (61) Cetiol 868 (7.25%) | 8.7 (3.0) |
| (62) Cetiol 868 (3.75%)/Velsan D8P3 (2.5%) | 14.2 (3.7) |
| (63) Mineral oil, NF (6.25%) | 6.7 (2.8) |
| (64) Mineral Oil, NF (3.75%)/Velsan D8P3 (2.5%) | 15.2 (3.8) |
| (65) Mineral Oil, NF (3.125%)/Citmol 316 (3.125%) | 4.3 (2.4) |
| (66) Mineral oil, NF (3.125%)/Minno 21 (3.125%) | 4.6 (2.1) |
| (67) Drakeol-7 (2.5%)/Miglyol 812 (3.75%) | 6.9 (2.9) |
| (68) Klearol (5.0%) | 11.0 (3.4) |
| (69) Klearol (2.5%)/Miglyol 812 (3.75%) | 6.6 (2.9), 5.4 (2.6), 7.0 (3.2), 7.7 (2.5) |
| (70) Arlamol E (6.25%) | 5.3 (2.2) |
| (71) Arlamol E (3.75%)/Velsan D8P3 (2.5%) | 14.3 (3.4) |
| (72) Dimethicone (6.25%) | 7.3 (3.0) |
| (73) Dimethicone (3.75%)/Velsan D8P3 (2.74%) | 14.1 (3.7) |
| (74) Dimethicone (2.5%)/Miglyol 812 (3.75%) | 3.5 (2.0) |
| (75) Miglyol 812 (3.0%)/Velsan D8P3 (2.5%) | 15.1 (3.5) |
| (75A) Eumulgin L (2.5%)/Miglyol 812 (3.75%) | 11.8 (2.8) |
| (76) Eumulgin L (6.25%)/Miglyol 812 (3.75%) | 11.2 (3.6) |
| (77) Crodamol ML (2.5%)/Miglyol 812 (3.75%) | 10.4 (3.0) |
| (78) Hetester PHA (2.5%)/Miglyol 812 (3.75%) | 13.1 (3.4) |
| (79) Procetyl 10 (2.5%)/Miglyol 812 (3.75%) | 9.5 (3.0) |
| (80) Marlox FK86 (2.5%)/Miglyol 812 (3.75%) | 11.0 (3.0) |
| (81) Ucon 50 HB-660 (2.5%)/Miglyol 812 (3.75%) | 9.4 (2.8) |
| (82) Eumulgin B-2 (2.5%)/Miglyol 812 (3.75%) | 12.5 (3.2) |
| (83) Eumulgin B-2 (6.25%) | 9.3 (3.0) |
| (84) Sandoxylate 424 (2.5%)/Miglyol 812 (3.75%) | 13.0 (3.4) |
| (85) Sandoxylate 418 (2.5%)/Miglyol 812 (3.75%) | 12.8 (3.1) |
| (86) Sandoxylate 412 (2.5%)/Miglyol 812 (3.75%) | 16.0 (3.3) |
| (87) Sandoxylate 408 (2.5%)/Miglyol 812 (3.75%) | 15.1 (3.3) |
| (88) UCON 50 HB-660 (2.5%)/Miglyol 812 (3.75%) | 9.4 (2.8) |
| (89) Velsan P83 (2.5%)/Miglyol 812 (3.75%) | 11.0 (3.0) |
| (90) Miglyol 812 (3.0%)/Velsan D8P3 (2.5%) | 15.1 (3.5) |

[1]Values in parentheses indicate protection factors in the UVA region of the spectrum.
[2]Multiple data indicate multiple independent formulation trials The brand names set forth above refer to the following commercially available compounds:

Eumulgin L: PPG-1-PEG-9 lauryl glycol ether
Hetester PHA: PG isoceteth-3-acetate
Sandoxylates: PPG-2 isodeceth (4 to 12)
Eumulgin B2: Ceteareth-20
Procetyl AWS: PPG-2 ceteth-20
Cetiol 868: Octyl stearate
Citmol 316: Triisocetyl citrate
Minno 21: Neopentyl glycol dioctanoate (and) neopentyl glycol
Drakeol-7: Mineral oil
Klearol: Mineral oil
Arlamol E: PPG-15 stearyl ether
Crodamol ML: Myristyl lactate
Procetyl 10: PPG-10 cetyl ether
Marlox FK86: PPG-8 deceth-6
Ucon 50 HB-660: PPG-12 buteth-16
Avanel S150: Sodium $C_{12-15}$ pareth-15 sulfonate
Velsan P8-3: Isopropyl $C_{12-15}$ pareth-9 carboxylate

EXAMPLES 91–94

In the following examples 91–94, the type of Velsan material was varied. Otherwise, the compositions are identical to that of Example 1.

TABLE V

**Effect of Velsan Type* on the SPF (with Constant Miglyol 812 at 3.75%)**

| | SPF[1,2] |
|---|---|
| (91) Velsan D8P3 | 15.3 (3.3) 21.0 (4.2) |
| (92) Velsan D8P16 (paste) | 12.6 (3.0) |
| (93) Velsan D8P16 (liquid) | 14.0 (3.4) |
| (94) Velsan P8-3 (liquid) | 14.0 (3.3) |

*Velsan level was 2.5%.
[1]Values in parentheses indicate protection factors in the UVA region of the spectrum.
[2]Multiple data indicate multiple independent formulation trials.

The brand names set forth above refer to the following commercially available compounds:

Velsan D8P16: Cetyl PPG-2 isodeceth-7 carboxylate
Velsan P8-3: Isopropyl $C_{12-15}$ pareth-9 carboxylate

EXAMPLE 95

A composition for use as a sunscreen was made, having components identical to those of Example 1, but in the oil phase was added 3% of octylmethoxycinnamate and the water adjusted down 3%. The resulting composition had an SPF of 23.3. Thus, it can be seen that the compositions of this invention may include organic as well as inorganic sunscreen agents.

EXAMPLE 96

A composition for use as a sunscreen was made, having components identical to those of Example 1, 5% of zinc oxide and 3% of Brij 721 were added. The resulting composition had an SPF of 20.4 with regard to UVB. The pH of the composition was adjusted to 7. This composition has a significantly enhanced protection value in UVB.

EXAMPLE 97

A composition for use as a sunscreen having anti-aging properties was made as follows. The formulation of this Example 97 contains the following ingredients:
Base formula with Retinol

|  | W/W % |
|---|---|
| WATER PHASE | |
| Deionized Water | 74.50 |
| Carbopol 940 | 0.25 |
| Propylene Glycol | 3.00 |
| Citric Acid | 0.10 |
| Sodium Stearate | 0.50 |
| Dowicil 200 | 0.10 |
| OIL PHASE | |
| BHT | 0.05 |
| Velsan D8P3 | 2.50 |
| Stearic Acid | 5.00 |
| Cetyl Alcohol | 1.00 |
| Miglyol 812 | 3.75 |
| Retinol (10% in Soybean Oil) | 1.65 |
| Tocopherol Acetate | 0.10 |
| Titanium Dioxide | 4.50 |
| Brij 721 | 3.00 |

The formulation of this Example was prepared as follows. The water phase was prepared by measuring formula weight of water into suitable vessel. Carbopol 940 was slowly introduced while mixing to allow the Carbopol 940 to become hydrated. Propylene glycol was then added followed by the sodium stearate and citric acid, and the phase mixed for 30 minutes. The mixture was then heated to 90° C. All oil phase ingredients were then combined separately with the exception of the retinol and were well mixed and then heated to 90° C. Under yellow light, Retinol was then added to the oil phase which was then added to the water phase and the system cooled while being mixed. Dowicil 200 was then added when the product reached 40° C. The entire mixture was then homogenized on a rotor-stator homogenizer for three minutes. The pH was then adjusted with sodium hydroxide to pH 6.42. The resulting product was then filled into aluminum tubes and purged with argon gas. The product may then be stored.

EXAMPLE 98

Comparative Example

The following composition 98A contained both inorganic and organic sunscreen agents. Composition 98B was made using the same formulation, but the organic sunscreen ingredients were removed. The formulations are as follows:

| Component | 98A % W/W | 98B % W/W |
|---|---|---|
| Deionized Water | 57.89 | 60.15 |
| Carbopol 940 | 0.40 | 0.40 |
| Propylene Glycol | 3.00 | 3.00 |
| Disodium EDTA | 0.10 | 0.10 |
| Carboset XL-19-X2 | 7.50 | 7.50 |
| Ammoniacal solution (7.5%) | 2.60 | 2.60 |
| Aerosol TO (75%) | 0.01 | — |
| Vitamin E Acetate | 0.10 | 0.10 |
| Isopropyl Isostearate | 2.50 | 2.50 |
| Butylated Hydroxytoluene | 0.05 | 0.05 |
| Finsolv TN | 5.00 | 5.00 |
| Velsan D8P3 | 2.50 | 2.50 |
| Dimethicone | 0.50 | 0.50 |
| Isostearic Acid | 2.00 | 2.00 |
| Cetyl Alcohol | 1.00 | 1.00 |
| Amphisol | 2.00 | 2.00 |
| Oxybenzone | 2.75 | — |
| Parsol MCX | 6.50 | — |
| Hombifine S-35 ($TiO_2$) | 1.00 | 3.96 |
| Octyl Salicylate | 1.00 | — |
| Lexamul GDL | 1.00 | 1.00 |
| Dowicil 200 (33% Solution) | 0.30 | 0.30 |
| Fragrance | 0.30 | 0.30 |
| Mineral Oil | — | 2.52 |
| Isopropyl Myristate | — | 2.52 |
| SPF | 20.2 | 2.4 |

As demonstrated by the foregoing SPF values, Formulation 98B, which did not contain any organic sunscreen agents, had an extremely low sun protection factor and was quite inefficient in its utilization of titanium dioxide. Thus, merely removing the organic sunscreen agents from Formulation 98A did not result in comparable SPF values.

EXAMPLE 99

Comparative Example

In this example, Formulation 99A contained isostearic acid, a branched-chain anionic emulsifier. Formulation 99B contained stearic acid, a straight-chain anionic emulsifier in accordance with the products of this invention. The formulations were as follows:

| Component | 99A % W/W | 99B % W/W |
|---|---|---|
| Deionized Water | 80.95 | 80.95 |
| Carpobol 940 | 0.40 | 0.40 |
| Propylene Glycol | 3.00 | 3.00 |
| Disodium EDTA | 0.10 | 0.10 |
| Vitamin E Acetate | 0.10 | 0.10 |
| Butylated Hydroxytoluene | 0.05 | 0.05 |
| Velsan D8P3 | 2.50 | 2.50 |
| Isostearic Acid | 5.00 | — |
| Stearic Acid | — | 5.00 |
| Cetyl Alcohol | 1.00 | 1.00 |
| Micro TiO2 SA-20 | 4.00 | 4.00 |
| Dowicil 200 (33% Sol'n) | 0.30 | 0.30 |
| Fragrance | 0.30 | 0.30 |
| D&C Red #33 (0.1% Sol'n) | 0.90 | 0.90 |
| Sodium Hydroxide (50% Sol'n) | 1.40 | 1.40 |
| SPF | 7.1 | 21.2 |

It can be seen that Formulation 99B, which contained stearic acid, a straight-chain anionic emulsifier in accordance with this invention, resulted in a considerably higher SPF than that of Formulation 99A, which contained isostearic acid, a branched-chain anionic emulsifier.

EXAMPLE 100

A sunscreen composition suitable for use as a dual-action carrier formulation was made containing the following materials:

| Component CTFA Name | % W/W |
|---|---|
| Deionized Water | 78.15 |
| Glycerin 99% | 3.00 |
| Carbopol 940 | 0.25 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide | 4.50 |
| Cetearyl Alcohol, Sodium Cetearyl Sulfate and Sodium Sulfate | 1.00 |
| Bisabolol | 0.20 |
| Butylated Hydroxytoluene | 0.05 |
| Sodium Hydroxide | Adjust pH to 7.5 |

The formulation of this Example 100 may be prepared as follows. The water phase was prepared by measuring formula weight of water into suitable vessel. Carbomer was slowly introduced while mixing to allow the Carbomer to become hydrated. The EDTA was then added, and the phase mixed for 30 minutes. After 30 minutes, the mixture was heated to 90° C. Glycerin and AMEA were then added to the phase. The BHT, Velsan D8P3, Stearic Acid, Cetearyl Alcohol and Caprylic/Capric Triglyceride and Bisabolol were then added. The temperature was held at 90° C. for fifteen minutes. The Titanium Dioxide was slowly added and the composition mixed for 30 minutes. The Sodium Hydroxide was added in solution form in order to adjust the pH to between 7 and 7.5. The solution was then mixed for 30 minutes at 88–92° C., forming the emulsion. The composition was then cooled to 35° C. and the pH again adjusted. Deionized water Was then added to replace evaporative loss and the batch homogenized for 5 minutes.

Additional formulations may be made in accordance with the process set forth in this Example 100 in order to create compositions according to this invention which contain one or more active ingredients in addition to the sunscreen. The carrier base of this invention affords a spreadable, cosmetically elegant composition in which to apply both sunscreen agents and additional topical active materials, as set forth below.

The following formulations may be produced according to the procedure set forth above in Example 100 with the understanding that the process may be adjusted to suit the specific materials. Adjustments may include, but are not limited to, pH of the final product, order of addition of raw materials and/or processing temperatures as necessary.

EXAMPLE 100A

Dihydroxyacetone-Containing (Sunless Tanning) Composition

| Component CTFA Name | % W/W |
|---|---|
| Deionized Water | 74.15 |
| Glycerin 99% | 3.00 |
| Carbopol 940 | 0.25 |
| Disodium Edetate | 0.10 |
| Aaetamide AMEA | 2.50 |
| Velsan D8P3 | 2.50 |
| Stearic Acid | 4.00 |
| Caprylic/Capric Triglyceride | 3.75 |
| Dihydroxyacetone | 4.00 |
| Titanium Dioxide MT 100T | 4.50 |
| Cetearyl Alcohol, Sodium Cetearyl Sulfate and Sodium Sulfate | 1.00 |
| Bisabolol | 0.20 |
| Butylated Hydroxytoluene | 0.05 |
| Sodium Hydroxide | Adjust pH to 7.5 |

EXAMPLE 100B

Composition Containing a Skin Whitening Agent, Magnesium Ascorbyl Phosphate

| Component CTFA Name | % W/W |
|---|---|
| Deionized Water | 75.15 |
| Glycerin 99% | 3.00 |
| Carbopol 940 | 0.25 |
| Disodium Edetate | 0.10 |
| Mag. Ascorbyl Phosphate | 3.00 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Bisabolol | 0.20 |
| Butylated Hydroxytoluene | 0.05 |
| Sodium Hydroxide | Adjust pH to 7.5 |

EXAMPLE 100C

Composition Containing a Skin Whitening Agent, Hydroquinone

| Component CTFA Name | % W/W |
|---|---|
| Deionized Water | 76.15 |
| Glycerin 99% | 3.00 |
| Carbopol 940 | 0.25 |
| Disodium Edetate | 0.10 |
| Hydroquinone | 2.00 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Bisabolol | 0.20 |
| Butylated Hydroxytoluene | 0.05 |
| Sodium Hydroxide | Adjust pH to 7.5 |

EXAMPLE 100D

Composition Containing Oil Soluble Retinoic Acid

| Component CTFA Name | % W/W |
|---|---|
| Deionized Water | 78.14 |
| Glycerin 99% | 3.00 |
| Carbopol 940 | 0.25 |
| Disodium Edetate | 0.10 |

-continued

| Component CTFA Name | % W/W |
|---|---|
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Retinoic Acid | 0.01 |
| Bisabolol | 0.20 |
| Butylated Hydroxytoluene | 0.05 |
| Sodium Hydroxide | Adjust pH to 7.5 |

EXAMPLE 100E

Composition Containing Oil-Soluble Retinaldehyde

| Component CTFA Name | % W/W |
|---|---|
| Deionized Water | 78.07 |
| Glycerin 99% | 3.00 |
| Carbopol 940 | 0.25 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Retinaldehyde | 0.08 |
| Bisabolol | 0.20 |
| Butylated Hydroxytoluene | 0.05 |
| Sodium Hydroxide | Adjust pH to 7.5 |

EXAMPLE 100F

Composition Containing Oil Soluble Retinol

| Component CTFA Name | % W/W |
|---|---|
| Deionized Water | 78.07 |
| Glycerin 99% | 3.00 |
| Carbopol 940 | 0.25 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Retinol | 0.08 |
| Bisabolol | 0.20 |
| Butylated Hydroxytoluene | 0.05 |
| Sodium Hydroxide | Adjust pH to 7.5 |

EXAMPLE 100G

Composition Containing Oil-Soluble Retinyl Palmitate

| Component CTFA Name | % W/W |
|---|---|
| Deionized Water | 77.35 |
| Glycerin 99% | 3.00 |
| Carbopol 940 | 0.25 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Retinyl Palmitate | 0.80 |
| Bisabolol | 0.20 |
| Butylated Hydroxytoluene | 0.05 |
| Sodium Hydroxide | Adjust pH to 7.5 |

EXAMPLE 100H

Composition Containing an Antifungal Agent

| Component CTFA Name | % W/W |
|---|---|
| Deionized Water | 76.15 |
| Glycerin 99% | 3.00 |
| Carbopol 940 | 0.25 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Ketoconazole | 2.00 |
| Bisabolol | 0.20 |
| Butylated Hydroxytoluene | 0.05 |
| Sodium Hydroxide | Adjust pH to 7.5 |

EXAMPLE 100J

Composition Containing an Antimicrobial Agent

| Component CTFA Name | % W/W |
|---|---|
| Deionized Water | 77.65 |
| Glycerin 99% | 3.00 |
| Carbopol 940 | 0.25 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Triclosan | 0.50 |
| Bisabolol | 0.20 |
| Butylated Hydroxytoluene | 0.05 |
| Sodium Hydroxide | Adjust pH to 7.5 |

EXAMPLE 100K

Composition Containing an "Insect Repellent" Fragrance

| Component CTFA Name | % W/W |
|---|---|
| Deionized Water | 72.15 |
| Glycerin 99% | 3.00 |

-continued

| Component CTFA Name | % W/W |
|---|---|
| Carbopol 940 | 0.25 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Cetearyl Alcohol, Sodium Cetearyl Sulfate and Sodium Sulfate | 1.00 |
| Insect Repellent Fragrance | 6.00 |
| Bisabolol | 0.20 |
| Butylated Hydroxytoluene | 0.05 |
| Sodium Hydroxide | Adjust pH to 7.5 |

EXAMPLE 100L

Composition Containing Iron Oxides

| Component CTFA Name | % W/W |
|---|---|
| Deionized Water | 76.49 |
| Glycerin 99% | 3.00 |
| Veegum | 0.60 |
| Disodium Edetate | 0.10 |
| Acetamide AMEA | 2.50 |
| Velsan D8P3 | 2.50 |
| Stearic Acid | 4.00 |
| Caprylic/Capric Triglyceride | 3.75 |
| Titanium Dioxide MT 100T | 4.50 |
| Iron Oxide | 1.66 |
| Cetearyl Alcohol, Sodium Cetearyl Sulfate and Sodium Sulfate | 1.00 |
| Keltrol | 0.40 |
| Bisabolol | 0.20 |
| Butylated Hydroxytoluene | 0.05 |
| Sodium Hydroxide | Adjust pH to 7.5 |

EXAMPLE 100M

Composition Containing an Alpha Hydroxy Acid

| Component CTFA Name | % W/W |
|---|---|
| Deionized Water | 55.95 |
| Carbopol 940 | 0.25 |
| Disodium Edetate | 0.10 |
| Sodium Stearate | 5.00 |
| Propylene Glycol | 3.00 |
| Butylated Hydroxytoluene | 0.05 |
| Velsan D8P3 | 2.50 |
| BRIJ 721 | 3.00 |
| Cetearyl Alcohol, Sodium Cetearyl Sulfate and Sodium Sulfate | 1.00 |
| Caprylic/Capric Triglyceride | 3.75 |
| Stearic Acid | 5.00 |
| Titanium Dioxide MT 100T | 4.50 |
| Glycolic Acid (70% solution) | 7.14 |
| Sodium Hydroxide (20% solution) | 8.66 |
| Dowicil 200 | 0.10 |

The pH of this product should be adjusted to about 5.15.

What is claimed is:

1. A sunscreen composition comprising:

(a) an inorganic sunscreen agent;

(b) an anionic emulsifier selected from the group consisting of salts of saturated fatty acids, salts of straight-chain fatty acids, alkyl sulfosuccinates, alkyl phosphates and mixtures thereof; and (c) an oil component comprising a carrier oil and at least one emollient.

2. A sunscreen composition according to claim 1 wherein said inorganic sunscreen agent is selected from the group consisting of titanium dioxide, zinc oxide and mixtures thereof.

3. A sunscreen composition according to claim 2 wherein said inorganic sunscreen agent is titanium dioxide.

4. A sunscreen composition according to claim 3 wherein said titanium dioxide has a primary particle size of less than about 30 nanometers.

5. A sunscreen composition according to claim 1 wherein said anionic emulsifier is a salt of a fatty acid.

6. A sunscreen composition according to claim 1 wherein said anionic emulsifier is selected from the group of sodium stearate, sodium lauryl sulfate, DEA cetyl phosphate, and dioctyl sodium sulfosuccinate.

7. A sunscreen composition according to claim 1 wherein said carrier oil is selected from the group consisting of benzoic acid fatty alcohol esters, polyalkoxylated fatty substances of the general formula $R-O_x-Po_y-EO_z$ wherein x=1, 2 or 3, y=0 to 4, z=6 to 20 with $R=C_8$ to $C_{15}$, and polyether interrupted fatty acid esters.

8. A sunscreen composition according to claim 7 wherein said polyether interrupted fatty acid ester is a $C_8$ to $C_{22}$ fatty alkyl (optionally polypropylenoxy) polyethylenoxy carboxylate ester, the ester having an alkyl group which has from one to twenty-two carbon atoms, optionally straight or branched.

9. A sunscreen composition according to claim 7 wherein said carrier oil is a benzoic acid fatty alcohol ester.

10. A sunscreen composition according to claim 7 wherein said carrier oil is a polyalkoxylated fatty substances of the general formula $R-O_x-Po_y-EO_z$ wherein x=1, 2 or 3, y=0 to 4, z=6 to 20 with $R=C_8$ to $C_{15}$.

11. A sunscreen composition according to claim 1 wherein said composition further comprises nonionic emulsifiers or mixtures thereof.

12. A sunscreen composition according to claim 1 wherein said composition has a pH of at least 5.

13. A sunscreen composition according to claim 12 wherein said pH is from about 7.5 to about 8.5.

14. A sunscreen composition according to claim 1 having a Sun Protection Factor of at least 10.

15. A method of making a sunscreen composition comprising:

(a) adding deionized water to a vessel;

(b) then, heating the water;

(c) then, adding a carrier oil and an anionic surfactant to the vessel;

(d) then, slowly adding an inorganic sunscreen agent to said vessel and heating and mixing said resultant composition; and (e) then, adjusting the pH of said composition to above 5.

16. A sunscreen composition comprising from about 2% to about 25% of an inorganic sunscreen agent, from about 0.5% to about 10% of an anionic emulsifier and from about 0.5 to about 10% of an oil component comprising a carrier oil and an emollient.

17. A sunscreen composition according to claim 1 wherein the ratio of inorganic sunscreen agent to oil component is from about 0.3:1 to about 1:1.

18. A sunscreen composition according to claim 1 wherein said composition further comprises one or more topically active agents.

19. A sunscreen composition according to claim 18 wherein said topically active agents are selected from the group consisting of: a sunless tanning agent, an organic sunscreen agent, an antimicrobial agent, a depigmentation agent, an anti-aging agent, an antifungal agent, an insect repellent and a combination thereof.

* * * * *